United States Patent [19]

Mauvernay

[11] 3,993,639
[45] Nov. 23, 1976

[54] HEPTAMINOL ADENOSINE-5'-MONOPHOSPHATE

[76] Inventor: Roland Yves Mauvernay, 13, rue Eugene Gilbert, 63201 Riom, France

[22] Filed: Feb. 5, 1975

[21] Appl. No.: 547,431

[30] Foreign Application Priority Data

Feb. 8, 1974 France .............................. 74.04237

[52] U.S. Cl. ................................. 536/27; 424/180
[51] Int. Cl.² ......................................... C07H 19/16
[58] Field of Search ............... 260/211.5 R; 424/180

[56] References Cited

UNITED STATES PATENTS

| | | |
|---|---|---|
| 2,710,860 | 6/1955 | Ruskins ......................... 260/211.5 R |
| 3,438,968 | 4/1969 | Glasky .......................... 260/211.5 R |
| 3,646,007 | 2/1972 | Gordon ......................... 260/211.5 R |
| 3,872,083 | 3/1975 | Okutsu et al. ................. 260/211.5 R |

*Primary Examiner*—Johnnie R. Brown
*Attorney, Agent, or Firm*—Haseltine, Lake & Waters

[57] ABSTRACT

The compound, heptaminol adenosine-5'-monophosphate, useful as a cardiovascular agent, is described.

1 Claim, No Drawings

HEPTAMINOL ADENOSINE-5'-MONOPHOSPHATE

This invention is concerned with a new chemical compound, the preparation thereof and pharmaceutical compositions containing it.

It has now been found, in accordance with the present invention that heptaminol adenosine-5'-monophosphate has interesting cardiovascular properties in man, notably in the treatment of venous vascular sufficiences, especially as a medicament which may be used in the treatment of phlebology.

Heptaminol adenosine-5'-monophosphate may be represented by the formula:

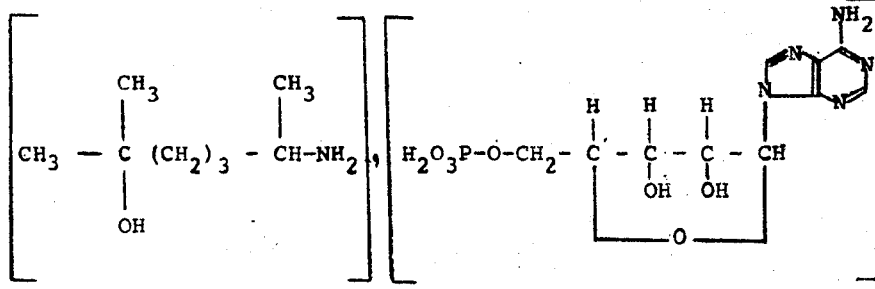

molecule, which is distinct from these two starting materials. In the second place, the cardiovascular activity of this new compound is markedly different from a simple addition of the activity observed with equivalent quantities of the two starting materials.

A comparative study between the compound of the invention and its two starting materials was made in the dog, the following parameters being noted:
Coronary sinusal flow rate,
Coronary sinusal $P_rO_2$,
Amplitude of right ventricular contractions,
Systemic arterial pressure, and
Pulse rate The results of this study are shown in Table 1 below:

TABLE 1

| Product | Dose mg/kg[1] | Number of Animals | Coronary Sinusal Flow Rate | Coronary Sinusal $P_rO_2$ | Systemic Arterial Pressure | Pulse Rate | Amplitude Of Left Ventricular Contractions |
|---|---|---|---|---|---|---|---|
| Product of the invention | 5 | 7 | + 51.1 | + 178.8 | − 50.4 | − 35.4 | + 51.9 |
| A.M.P. | 3.65 | 6 | + 68.5 | + 93.7 | − 40.3 | − 46.2 | + 6.8 |
| HEPTAMINOL | 1.35 | 6 | 0 | 0 | + 11.2 | − 9.9 | + 86.8 |

[1] The doses/kg used for A.M.P. and HEPTAMINOL represent the amount of each of these products contained in 5mg/kg of the product of the invention The new compound in accordance with the invention may be prepared by reacting equimolar amounts of heptaminol and adenosine-5'-monophosthonic acid (hereinafter referred to as AMP). The following example illustrates the preparation of heptaminol adenosine-5'-monophosphate.

EXAMPLE 145.24 Grams (1 mole) of heptaminol are dissolved in the cold in 1,000 ml of distilled water and then 347.23 grams (1 mole) of anhydrous (AMP) are added progressively to the solution. After a few minutes, when the solution has become homogenous, it is frozen and the ice is then sublimed for a period of about 12 hours by stoving under vacuum at about 40° C.

The product is a solid obtained in the form of a white powder which is soluble in water and insoluble in organic solvents. The compound has a melting point, as measured by the capillary tube method, of 118± 1° C. The UV spectrum of a 1% solution shows a coefficient of extension at 261 nm of 300± 15. The product has the following analyses:

Calculated C, 43.89%; H, 6.75%; N, 17.06%. Found C, 43.59%; H, 7.33%; N, 17.53%.

It should be noted that the new compound, comprising a combination of two portions well known for their respective properties, is indubitably distinguished from a simple mixture of these two portions.

Thus, in the first place, examination of the physico-chemical constant confirms the existence of a new The following comments may be made a result of the above results.

In the first case, for each of the parameters noted, the activity of the compound of the invention does not correspond to a simple addition of the effects of AMP and heptaminol. On the contrary, for example, the variation in coronary per rate is notably less with the compound of the invention than with AMP whilst heptaminol has no effect. Further, the variation in ventricular inotropism is considerably less with the compound of the invention than with heptaminol whilst AMP exercises a positive activity on this factor. These differences, which cannot be explained, clearly show that the compound of the invention is a definite compound and not a simple mixture.

In the second place, there should be noted the very important increase in sinusal $P_rO_2$ obtained with the compound of the invention although this parameter is not affected by heptaminol and is very much less improved by AMP. This improvement in the balance of oxygen in the myocardic effluent blood is not the detriment of the cardiac dynamic since the compound according to the invention stimulates the amplitude and frequency of the cardiac contractions at the same time as it increases the arterial pressure.

The compound in accordance with the invention may, as a result of these properties, be used in human medicine, notably in phlebology in the treatment of neurocirculatory asthenia, fatigue and all conditions indicating a cerebral circulatory insufficiency, such as vertigo, headache and buzzing in the ear.

Accordingly, the invention also provides a pharmaceutical composition comprising the compound in accordance with the invention in association with one or more pharmaceutical carriers or diluents. The carriers or diluents may be liquid or solid and thus, where they are liquid, the compositions of the invention may take the form of solutions, suspensions, syrups, linctuses etc.. Where the carrier is a solid the compositions of the invention may take the form of pills, tablets, dragees etc...

Among the possible applications of the composition of the invention, phlebology represents a particular interest and for this reason are given below the results of chemical trials carried out with the compositions of the invention and administered in capsules containing 300 mg of active ingredient. These capsules were prepared by mixing the following components in the following proportions.

| | |
|---|---|
| Product of the invention | 300 mg |
| Corn starch | 190 mg |
| Magnesium stearate | 5 mg |

-continued

| | |
|---|---|
| Talc | 10 mg |

The product of the invention was mixed with the corn starch in a cubic mixer until complete homogenity was obtained. The talc and magnesium stearate were then added to the mixture which was then placed in capsules of size zero.

The product was tested clinically at doses of from 4 to 6 capsules per day on patients suffering from various venus pripheric vascular conditions.

The compound was found to be particularly interesting as shown in Table II below.

TABLE II

| | Aches | Dullness | Cramps | Odemas |
|---|---|---|---|---|
| Number of cases | 30 | 28 | 29 | 22 |
| Success (++) | 22 (73%) | 20 (71%) | 21 (72%) | 16 (72%) |
| Useful Result (+) | 2 (7%) | 4 (14%) | 2 (7%) | 1 (4%) |
| Result questionable or nil (O) | 6 (20%) | 4 (14%) | 6 (20%) | 5 (23%) |

What we claim is:
1. Heptaminol adenosine-5'-monophosphate.

* * * * *